United States Patent [19]
Feenstra et al.

[11] Patent Number: 6,090,812
[45] Date of Patent: Jul. 18, 2000

[54] PIPERAZINE AND PIPERIDINE COMPOUNDS

[75] Inventors: Roelof Willem Feenstra; Jacobus A. J. Den Hartog; Cornelis G. Kruse; Martinus T. M. Tulp; Stephen K. Long, all of Weesp, Netherlands

[73] Assignee: Duphar International Research B.V., Weesp, Netherlands

[21] Appl. No.: 09/158,520

[22] Filed: Sep. 22, 1998

[30] Foreign Application Priority Data

Sep. 24, 1997 [EP] European Pat. Off. .............. 97202950

[51] Int. Cl.$^7$ ....................... C07D 295/12; A61K 31/496
[52] U.S. Cl. ......................... 514/254.1; 544/364
[58] Field of Search .............. 544/364; 514/254

[56] References Cited

U.S. PATENT DOCUMENTS 5,436,246  7/1995  Bernotas et al. .

FOREIGN PATENT DOCUMENTS

| | | |
|---|---|---|
| 633260 | 1/1995 | European Pat. Off. . |
| 19637237 | 3/1998 | Germany . |
| WO 93/04684 | 3/1993 | WIPO . |
| WO 95/02592 | 1/1995 | WIPO . |
| WO 97/36893 | 10/1997 | WIPO . |
| 98/11068 | 3/1998 | WIPO . |

OTHER PUBLICATIONS

Van Steen et al., "Structure–Affinity Relationship Studies on 5–HT1A receptor Ligands. 2. Heterobicyclic Phenylpiperazines With N4–Aralkyl Substituents", J. Med. Chem., 37(17):2761–2773 (1994).

*Primary Examiner*—Robert Gerstl
*Attorney, Agent, or Firm*—Finnegan, Henderson, Farabow, Garrett & Dunner, L.L.P.

[57] ABSTRACT

A group of new piperazine and piperidine compounds having interesting advantageous pharmacological properties and have the formula (a)

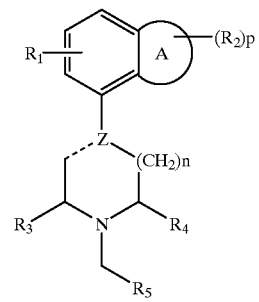

wherein
A represents a heterocyclic group having 5–7 ring atoms wherein 1–3 heteroatoms selected from the group O, N and S are present,
$R_1$ is hydrogen or fluoro,
$R_2$ is $C_{1-4}$-alkyl, $C_{1-4}$-alkoxy or an oxo group, and p is 0, 1 or 2,
Z represents carbon or nitrogen, and the dotted line represents a single bond when Z is nitrogen, and represents a single or double bond when Z is carbon,
$R_3$ and $R_4$ independently are hydrogen or $C_{1-4}$-alkyl,
n has the value 1 or 2,
$R_5$ is 2-pyridyl, 3-pyridyl or 4-pyridyl substituted at the meta-position with respect to the methylene bridge with a group Y, and optionally substituted with $(R_6)q$,
Y is a phenyl, furanyl or thienyl group, which groups may be substituted with 1–3 substituents from the group hydroxy, halogen, $CF_3$, $C_{1-4}$-alkoxy, $C_{1-4}$-alkyl, cyano aminocarbonyl, mono- or di-$C_{1-4}$-alkylaminocarbonyl,
$R_6$ is halogen, hydroxy, $C_{1-4}$-alkoxy or $C_{1-4}$-alkyl, and q is 0, 1, 2 or 3 and salts thereof, are disclosed.

9 Claims, No Drawings

PIPERAZINE AND PIPERIDINE COMPOUNDS

The invention relates to a group of new piperazine and piperidine compounds having interesting pharmacological properties. The inventors have discovered that compounds of the formula (a)

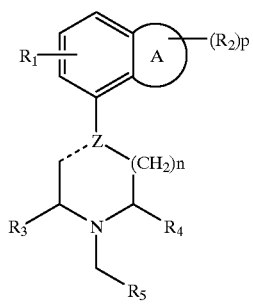

(a)

wherein
- A represents a heterocyclic group having 5–7 ring atoms, wherein 1–3 heteroatoms selected from the group O, N and S are present,
- $R_1$ is hydrogen or fluoro,
- $R_2$ is $C_{1-4}$-alkyl, $C_{1-4}$-alkoxy or an oxo group, and p is 0, 1 or 2,
- Z represents carbon or nitrogen, and the dotted line represents a single bond when Z is nitrogen, and represents a single or double bond when Z is carbon,
- $R_3$ and $R_4$ independently are hydrogen or $C_{1-4}$-alkyl,
- n has the value 1 or 2,
- $R_5$ is 2-pyridyl, 3-pyridyl or 4-pyridyl substituted at the meta-position with respect to the methylene bridge with a group Y, and is optionally substituted with $(R_6)q$,
- Y is a phenyl, furanyl or thienyl group, which groups may be substituted with 1–3 substituents selected from the group hydroxy, halogen, $CF_3$, $C_{1-4}$-alkoxy, $C_{1-4}$-alkyl, cyano, aminocarbonyl, mono- and di-$C_{1-4}$-alkylaminocarbonyl,
- $R_6$ is halogen, hydroxy, $C_{1-4}$-alkoxy or $C_{1-4}$-alkyl, and q is 0, 1, 2 or 3, and the salts thereof have interesting and advantageous pharmacological properties.

Preferred compounds according to the invention are the compounds of formula (a) wherein A together with the phenyl group represents a group of the formula b, c, d, e, f or g

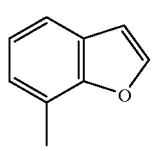

b

-continued c d e f g wherein n is 1 and $R_1$ and $(R_2)p$, $R_3$, $R_4$, $R_5$, $(R_6)_q$, Y and Z have the above meanings, and the salts thereof.

Particularly preferred are the inventive compounds of formula (a) wherein A together with the phenyl group represents a group of the formula (c) or (d), $R_5$ has the above meaning and Y is phenyl which may be substituted as mentioned above, and wherein $R_2$ has the above mentioned meaning, p=0 or 1, n is 1, $R_3$ and $R_4$ are hydrogen, $R_6$ is hydroxy, methoxy or halogen, q is 0 or 1, Z is nitrogen, and the salts thereof.

Particularly preferred is the compound having formula (a) wherein A together with the phenyl group represents the group of the formula (d), wherein $R_1$, $(R_2)_p$, $R_3$ and $R_4$ are hydrogen, n is 1, Z is nitrogen, and $R_5$ is the group 5-(4-fluorophenyl)-pyrid-3-yl, and the salts thereof.

It is known from EP 0650964 that compounds of the formula

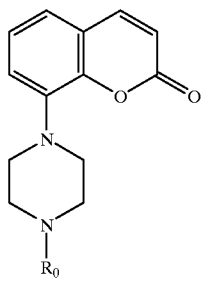

wherein $R_0$ is $C_{1-4}$-alkyl, which compounds can be substituted in the phenyl group and/or heterocyclic group and/or the piperazine group, act on the central nervous system by binding to 5-HT receptors. In particular these compounds bind to subtypes of the 5-HT-receptor, i.e. $5\text{-}HT_{1A}$ and $5\text{-}HT_{1D}$ receptors.

It has now surprisingly been found that the compounds according to the invention show affinities for the dopamine $D_2$ receptor ($pK_i$ range 7–9.5) and dopamine $D_4$ receptor ($pK_i$ range 6.5–9.5) without significant preference for one of the above mentioned two receptors. Moreover, the compounds according to the invention show affinity for serotonin $5\text{-}HT_{1A}$ receptors ($pK_i$ range 7–9.5). This combination of affinities for dopamine and serotonin receptors is useful for the treatment of schizophrenia and other psychotic disorders and might allow for a more complete treatment of all disease symptoms, e.g., positive symptoms, negative symptoms and cognitive deficits.

The inventive compounds also show varying activities as either partial agonists or antagonists at dopamine $D_2$-, $D_3$-, and $D_4$- receptors. Some inventive compounds show agonist-like effects at dopamine receptors, however they potently antagonize apomorphine-induced climbing behavior in mice ($ED_{50}$ values<1 mg/kg p.o). The inventive compounds further show varying activity as $5\text{-}HT_{1A}$ receptor agonists and induce aspects of the serotinin behavioral syndrome to differing intensities.

The inventive compounds are active in therapeutic models sensitive to clinically relevant antipsychotics (e.g., the conditioned avoidance response; Van der Heyden & Bradford, Behav. Brain Res., 1988, 31:61–67, the disclosure of which is incorporated herein by reference), antidepressants (e.g., differential reinforcement of low rate responses; van Hest et al., Psychopharmacology, 1992, 107:474–479, the disclosure of which is incorporated herein by reference), and anxiolytics (e.g., suppresion of stress-induced vocalization; van der Poel et al., Psychopharmacology, 1989, 97:147–148, the disclosure of which is incorporated herein by reference).

In contrast to clinically relevant dopamine $D_2$ receptor antagonists, the described compounds have a low propensity to induce catalepsy in rodents and as such are likely to induce less extrapyramidal side effects than existing antipsychotic agents.

The $^5\text{-}HT_{1A}$ receptor agonism inherent in the inventive compounds may be responsible for the reduced tendency to induce extrapyramidal effects and the therapeutic effects observed in behavioral models sensitive to either antidepressants or anxiolytics.

The inventive compounds are additionally expected to be of value for the treatment of affective disorders or diseases of the central nervous system caused by disturbances in either the dopaminergic or serotinergic systems, for example: Parkinson's disease, aggression, anxiety disorders, autism, vertigo, depression, disturbances of cognition or memory, and in particular schizophrenia and other psychotic disorders.

Suitable acids with which the inventive compounds can form pharmaceutically acceptable acid addition salts are, for example, hydrochloric acid, sulphuric acid, phosphoric acid, nitric acid, and organic acids such as citric acid, fumaric acid, maleic acid, tartaric acid, acetic acid, benzoic acid, p-toluene sulphonic acid, methanesulphonic acid and naphtalene-sulphonic acid.

The compounds of the invention can be brought into forms for administration by means of well known processes using auxiliary substances such as liquid and solid carrier materials.

The compounds of the invention can be obtained according to methods (A and B) which are described below. The piperazines used in these methods are indicated as I-H to III-H, wherein I to III represent the following groups:

FIG. 1

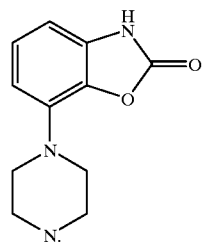

I

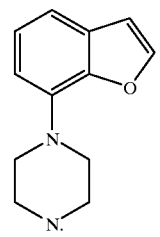

II

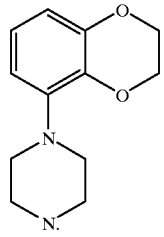

III

The synthesis of these piperazines I-H to II-H is described in EP 0189612, the disclosure of which is incorporated herein by reference.

The H-atom of the N—H moiety of compounds I-H to III-H can be replaced by group Q in two different chemical ways (A and B), eventually leading to the compounds of the invention. In FIG. 2, the meanings of Q1 to Q9 are shown.

FIG. 2

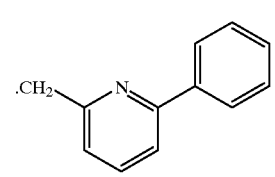

1

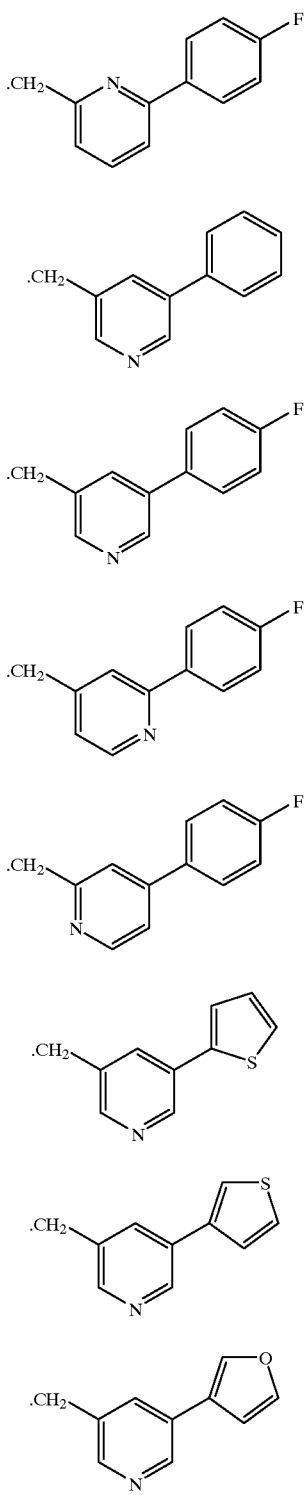

Synthesis route A

The compounds listed in table A (vide infra) were prepared via the synthesis depicted in scheme A1 (vide infra): a piperazine was reacted with a compound Q—X (X=Cl, Br) in e.g., acetonitrile with Et(i-Pr)$_2$N acting as a base; in some cases KI (or NaI) be used instead of Et(i-Pr)$_2$N.

Synthesis route B

The compounds listed in table B (vide infra) were prepared via the synthesis depicted in scheme Bi (vide infra): a piperazine was reacted with 3-bromo-5-chloromethyl-pyridine to yield the intermediate b1 (scheme B2), which was coupled with a boronic acid derivative by means of a so-called Suzuki cross-coupling reaction.

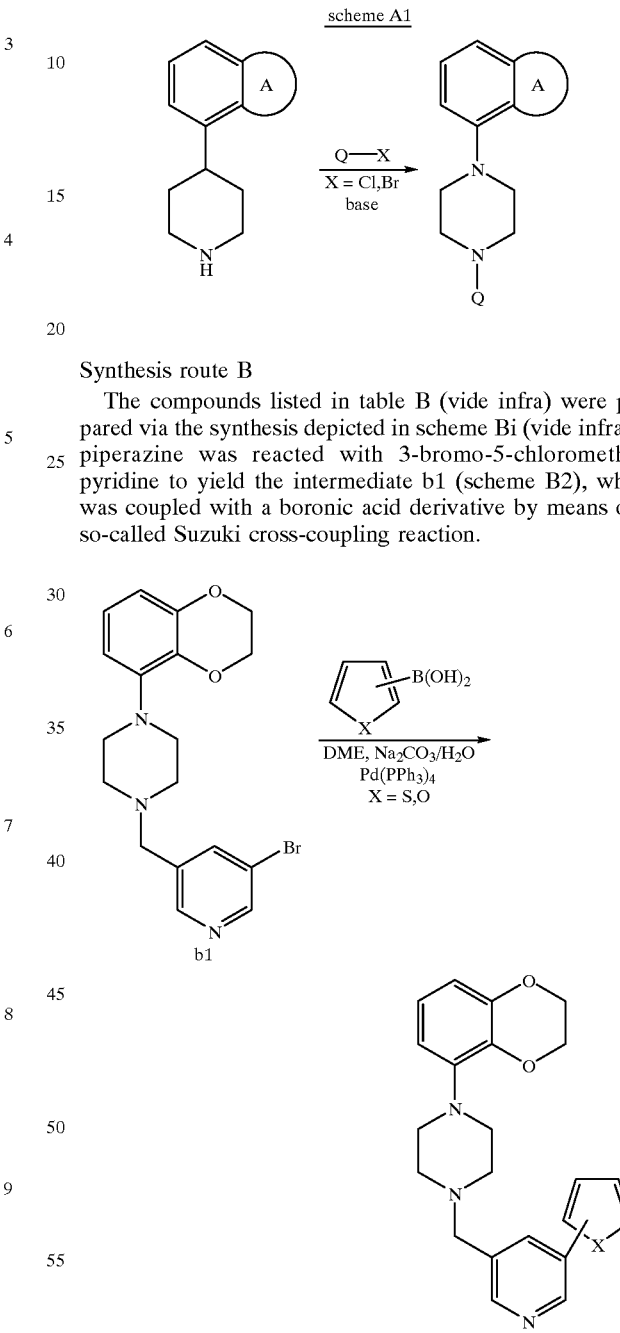

A preferred method for preparing a compound of the formula (a) as defined above, comprises either reacting a compound of formula

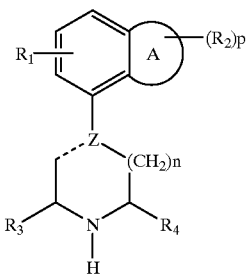

with a compound of the formula $R_5$—$CH_2$—X, wherein X is a leaving group and the remaining substituents $R_1$, $R_2$, $R_3$, $R_4$, Z, A, p, n and $R_5$ are as defined above for formula (a), or reacting a compound of formula

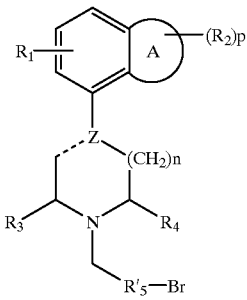

wherein $R_5'$ has the same meaning as $R_5$ given above in formula (a), with the proviso that the bromine atom is at the meta-position with respect to the methylene bridge, with a compound of the formula $B(OH)_2$—Y, wherein B and Y have the same meanings as given in formula (a) above.

The preparation of the compounds of formula (a) and of a number of intermediate compounds will now be described in detail in the following nonlimiting

EXAMPLES

Example 1
Procedure A1 (scheme A1):

To a suspension of 1-(2,3-dihydro-1,4-benzodioxin-5-yl) piperazine monohydrochloride III-H.HCl (1.1 g, 4.25 mmol) in $CH_3CN$ (40 ml) was added Q4-Cl (1.0 g, 3.87 mmol) and diisopropylethylamine (2.45 g, 19 mmol). The mixture was stirred at reflux for 3 hrs. After cooling and evaporation of the solvent in vacuo, the residue was taken up in $CH_2Cl_2$, washed with 5% $NaHCO_3$ solution, saturated NaCl, dried ($Na_2SO_4$), filtered, and evaporated in vacuo. The resulting dark oil was purified by flash chromatography on silica gel ($CH_2Cl_2$/MeOH/$NH_4OH$, 97.25 /2.5/0.25) to give A8 (0.9 g, 58%) as an oil. The product was converted to its monohydrochloride salt; the residue was dissolved in $Et_2O$ and treated with 1 eq. of ethanolic HCl. The product precipitated as a white solid. The solid A8.HCl was collected by filtration and dried: mp 233–5° C., dec; $^1H$ NMR (400 MHz, DMSO/CDCl$_3$, 4/1) δ (ppm) 3.1–3.6 (cluster, 8H), 4.24 (m, 4H), 4.58 (s, 2H), 6.49 (d, 1H, J=8 Hz), 6.55 (d, 1H, J=8 Hz), 6.74 (t, 1H, J=8 Hz), 7.34 (m, 2H), 7.91 (m, 2H), 8.77 (m, 1H), 8.9 (m, 1H), 9.10 (m, 1H), 11.8 (br s, 1 H, NH$^+$).

Example 2
Procedure A1 (scheme A1):

A suspension of 2-(p-fluorophenyl)-4-bromomethylpyridine Q5-Br (0.71 g, 2.67 mmol), and 1-(2-benzoxazolinone-4-yl) piperazine I-H.HCl (0.58 g, 2.27 mmol) in DMF (20 ml) together with 2.1 equivalents of $Et_3N$ was stirred at room temperature for 2 h. The resulting clear solution was concentrated to give a red oil which was purified by flash column chromatography ($SiO_2$, eluting with $CH_2Cl_2$/MeOH/$NH_4OH$, 92/7.5/0.5) to give A9 (0.28 g, 26%) as a yellow solid: mp 213–4° C.; $^1H$ NMR (400 MHz, DMSO/CDCl$_3$, 4/1) δ (ppm) 2.62 (m, 4H), 3.24 (m, 4H), 3.64 (s, 2H), 6.59 (d, 1 H, J=8 Hz), 6.63 (d, 1H, J=8 Hz), 7.01 (t, 1H, J=8 Hz), 7.27 (m, 2H), 7.32 (m, 1H), 7.85 (m, 1H), 8.13 (m, 2H), 8.6 (m, 1H), 11.5 (s, 1H).

According to the syntheses given above, the other compounds A1–A12 were prepared in a similar way.

TABLE A

| compound | piperazine | Q | X | salt | melting point ° C. |
|---|---|---|---|---|---|
| A1 | II | 1 | Cl | fb | 105–6 |
| A2 | III | 1 | Cl | fb | 125–6 |
| A3 | II | 2 | Cl | fb | 132–3 |
| A4 | I | 2 | Cl | fb | 233–5 |
| A5 | III | 3 | Cl | HCl | 208 |
| A6 | I | 4 | Cl | fb | 214–5 |
| A7 | I | 3 | Cl | fb | 172–3 |
| A8 | III | 4 | Cl | HCl | 233–5 d |
| A9 | I | 5 | Br | fb | 213–4 |
| A10 | III | 5 | Br | 2HCl | 162 d |
| A11 | III | 6 | Cl | 2HCl | 223 d |
| A12 | I | 6 | Cl | 2HCl | 270–5 d | fb = free base,
d = decomposition

Example 3
Procedure B1 (scheme B1)

A solution of b1 (1.07 g, 2.75 mmol) and Pd(PPh$_3$)$_4$ (0.1 g, 0.08 mmol) in DME (5 ml) was stirred at room temperature for 10 minutes under a $N_2$ atmosphere. Then 2-thiopheneboronic acid (0.39 g, 3.0 mmol) and an aqueous solution of $Na_2CO_3$ (2.75 ml of a 2M solution) were consecutively added and the mixture was allowed to react at reflux temperature for 1 hr. The solution was cooled, diluted with $H_2O$, and extracted with $CH_2Cl_2$. The organic phase was evaporated to dryness in vacuo to give the crude product B1, which was purified by flash chromatography ($CH_2Cl_2$/MeOH, 98/2) and then converted to its monohydrochloride salt to obtain B1.HCl (0.8 g, 74%) as a white solid: mp 160° C., dec., material turned sticky; $^1H$-NMR (400 MHz, CDCl$_3$) δ (ppm) 3.0–3.8 (br b , 8H, NH$^+$, $H_2O$), 4.25 (m, 4H), 4.63 (br s, 2H), 6.54 (d, 1H, J=8 Hz), 6.64 (d, 1H, J=8 Hz), 6.75 (t, 1H, J=8 Hz), 7.14 (m, 1H), 7.43 (d, 1H, J=5 Hz), 7.74 (m, 1H).

According to the synthesis given above, the compounds B2–B3 were preprared in a similar way.

TABLE B

| compound | piperazine | Q | salt | melting point ° C. |
|---|---|---|---|---|
| B1 | III | 7 | HCl | turns sticky at 160 |
| B2 | III | 8 | HCl | 224–5 |
| B3 | III | 9 | HCl | 238–9 |

Intermediates used in route A

Intermediates Q—X:
Q1-Cl:
This intermediate was synthesized as depicted in scheme A2:

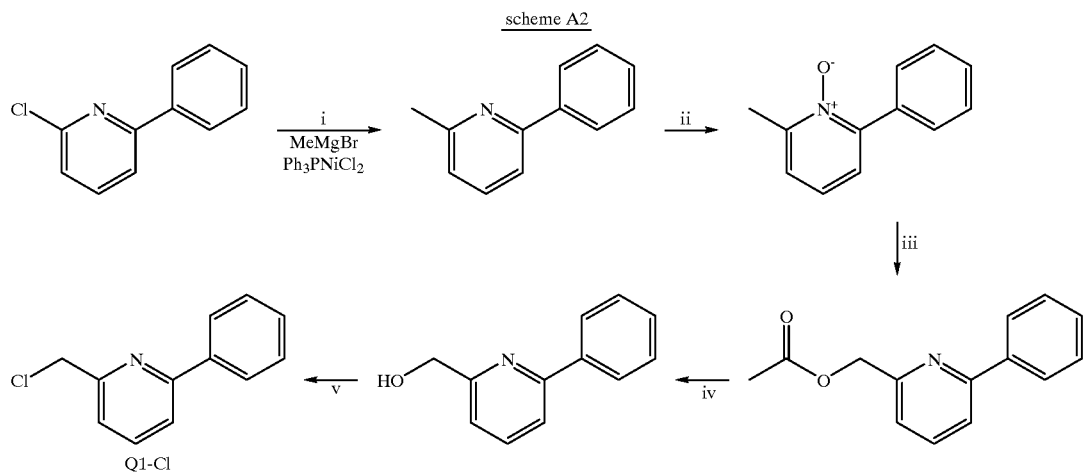

scheme A2

Step i (scheme A2):
This step was carried out analogously to the procedure described in *J. Het. Chem.*, 12, (1975), 443, the disclosure of which is incorporated herein by reference.

Step ii (scheme A2):
While stirring at room temperature, 4.8 g (28.5 mmol) of 2-phenyl-6-methyl-pyridine were dissolved in 50 ml of chloroform after which a solution of 7.8 g of 75% mCPBA (33.9 mmol) in 75 ml of chloroform were added dropwise. The reaction mixture showed only a slight rise in temperature. After stirring for 1.5 hr, the reaction mixture was shaken twice with 5% aqueous $NaHCO_3$ solution and twice with an aqueous solution of $Na_2S_2O_3$ to remove the excess of mCPBA, after which the reaction mixture proved to be negative on wet KI/starch paper, The organic layer was dried on $MgSO_4$. Removal of the drying agent by filtration and solvent by evaporation in vacuo yielded an oil which crystallized upon scratching to give 5.5 g (105%) of crude of 2-phenyl-6-methyl-pyridine-N-oxide, which was employed in the next step without further purification.

Step iii (scheme A2):
A stirred solution of the crude 2-phenyl-6-methyl-pyridine-N-oxide (5.2 g, 28.5 mmol) in $Ac_2O$ (25 ml) was heated at reflux temperature for 2 hrs. The $Ac_2O$ was removed with the aid of an oil pump (10 mm) at 40° C. to yield a red oil which was purified by flash chromatography over silica gel with $Et_2O$/petroleum benzine=1/1 as the eluent and yielded 2-phenyl-6-(acetoxymethyl)-pyridine (4.6 g, 70%) as an oil.

Step iv (scheme A2:)
4.5 g of 2-phenyl-6-(acetoxymethyl)-pyridine (20 mmol) was treated with an aqueous HCl solution (15%, 10 ml) and the mixture was heated at reflux temperature while stirring.

After 30 minutes the reaction mixture was concentrated with the aid of an oil pump (10 mm) at 40° C., $CH_3CN$ was added, and the mixture was evaporated to dryness in vacuo and yielded 2-phenyl-6-(hydroxymethyl)-pyridine (3.0 g, 80%) as an oil.

Step v (scheme A2):
To a stirred solution of 2-phenyl-6-(hydroxymethyl)-pyridine (1.0 g, 5.4 mmol) in $CHCl_3$ (7 ml) at room temperature was added dropwise $SOCl_2$ (1.22 g, 10.2 mmol) and the mixture was heated at 60° C. for 20 minutes. After evaporation of the solvent in vacuo, the residue was purified by trituration with $Et_2O$. The resulting precipitate was collected by filtration and dried to give 2-phenyl-6-(chloromethyl)-pyridinium chloride Q1-Cl (1.2 g, 92%) as a white solid.

Q2-Cl:
Q2-Cl was prepared analogously to the synthesis of Q1-Cl.

Q3-Cl
Q3-Cl was prepared analogously to the synthesis of Q4-Cl (vide infra).

Q4-Cl:
This intermediate was synthesized as depicted in scheme A3:

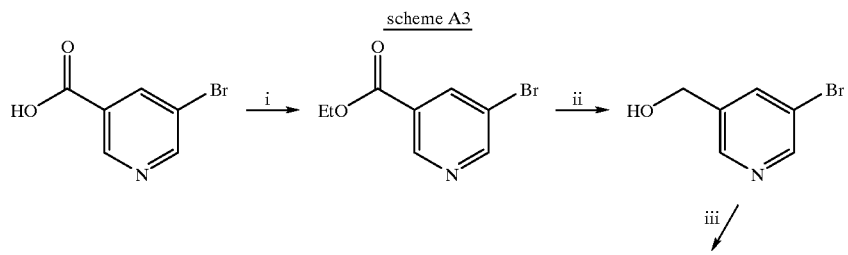

scheme A3

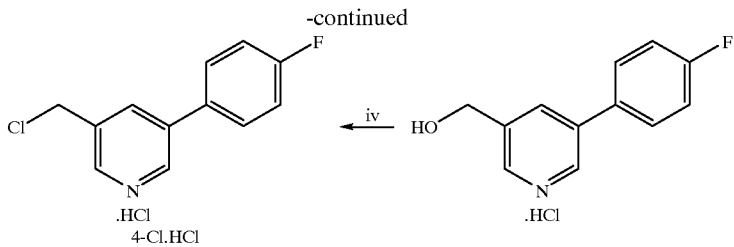

Step i (scheme A3);

A stirred mixture of 3-bromo-5-pyridine-carboxylic acid (10.1 g, 50 mmol) and $H_2SO_4$ (1.5 ml) in EtOH (150 ml) was refluxed for 6 hrs. After cooling, the solvent was removed by evaporation in vacuo. The residue was diluted with $H_2O$ (100 ml), basified with 5% $NaHCO_3$ (aq) solution and extracted with ether (4×100 ml). The combined organic extracts were washed with saturated NaCl and dried over $Na_2SO_4$. Filtration and concentration in vacuo of the filtrate yielded 3-bromo-5-pyridine-carboxylic acid ethyl ester as an oil that solidified on standing: (9.8 g, 85%).

Step ii (scheme A3):

To a stirred solution of 3-bromo-5-pyridine-carboxylic acid ethyl ester (9.5 g, 41.3 mmol) in EtOH (96%, 220 ml), $NaBH_4$ (14.4 g, 380 mmol) was added slowly at 25° C.

The reaction was mildly endothermic. The mixture was stirred under an nitrogen atmosphere at room temperature for 6 hrs. The resulting milky mixture was diluted with $H_2O$ (150 ml), the EtOH was evaporated in vacuo and the residue was extracted with $CH_2Cl_2$ (3×). The combined organic layers were dried on $Na_2SO_4$. After filtration the filtrate was concentrated in vacuo to give 9 g of a crude oil which was purified by flash chromatography on silica gel (eluent: $Et_2O$) to give 3-bromo-5-hydroxymethyl-pyridine (3.5 g, 45%).

Step iii (scheme A3):

To a solution of 3-bromo-5-hydroxymethyl-pyridine (3.3 g, 17.5 mmol) in toluene (35 ml) was added $Pd(PPh_3)_4$ (0.6 g, 0.52 mmol), an aqueous solution of $Na_2CO_3$ (17.5 ml of a 2M solution) and p-fluorphenylboronic acid (2.65 g, 19 mmol, dissolved in 8.5 ml EtOH). The mixture was heated at 80–90° C. for 1 hr and vigorously stirred. After the reaction was completed, the biphasic reaction mixture was cooled, the organic layer was collected and washed with saturated NaCl. The aqueous layer was washed with EtOAc and the combined organic layers were dried on $Na_2SO_4$. The drying agent was removed by filtration and the solvent was evaporated in vacuo to give a dark oil which was purified by flash chromatography on silica gel (eluent: $CH_2Cl_2$/MeOH/ $NH_4OH$, 95/4.5/0.5) and yielded 3-(p-fluorophenyl)-5-hydroxymethyl-pyridine (3.0 g, 84%). The product was converted into its monohydrochloride salt; the residue was dissolved in $Et_2O$ and treated with 16.5 eq of ethanolic HCl. The product 3-(p-fluorophenyl)-5-hydroxymethyl-pyridinium hydrochloride Q4-OH.HCl precipitated as a white solid which was collected by filtration and subsequent drying.

Step iv (scheme A3):

3-(p-fluorophenyl)-5-hydroxymethyl-pyridinium hydrochloride Q4-OH.HCl (3.5 g, 14.7 mmol) was added to an excess of $SOCl_2$ (20 ml) and the mixture was heated at 60° C. to start the reaction (generation of HCl). After complete conversion of the starting material (45 min), the reaction mixture was cooled and excess $SOCl_2$ was removed in vacuo to leave a dry residue. Crystallization from $Et_2O$ provided 3-(p-fluorophenyl)-5-chloromethyl-pyridinium hydrochloride Q4-Cl.HCl (2.5 g, 66%).

Q5-Br:

The synthesis of Q5-Br is depicted in scheme A4:

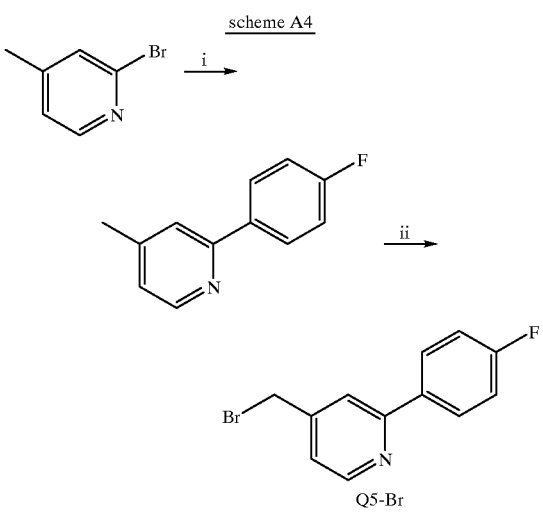

Step i (scheme A4):

A solution of 2-bromo-4-methyl-pyridine (10 g, 58 mmol) and $Pd(PPh_3)_4$ (1.5 g, 1.3 mmol) in toluene (110 ml) was stirred at room temperature under a nitrogen atmosphere. Subsequently an aqueous solution of $Na_2CO_3$ (58 ml of a 2M solution) and p-fluorophenylboronic acid (8.93 g, 63.8 mmol) were added and the resulting mixture was allowed to react at 90–100° C. for 4 hrs. The mixture was cooled, the aqueous layer was separated and extracted with EtOAc (2×). The combined EtOAc and toluene fractions were dried on $MgSO_4$. Filtration of the drying agent and removal of the solvent in vacuo yielded a pink oil (28 g). Distillation gave pure 2-(p-fluorophenyl)-4-methyl-pyridine (6.10 g, 56%); bp 110–116° C. (6–7 mbar) as a colorless oil.

Step ii (scheme A4):

A mixture of 2-(p-fluorophenyl)-4-methyl-pyridine (0.5 g, 2.67 mmol), N-bromosuccinimide (0.48 g, 2.69 mmol), and a catalytic amount of benzoylperoxide in $CCl_4$ (50 ml) was stirred at reflux temperature and irradiated by means of an ordinary 250-W UV lamp for 4 hrs. Afterwards, the reaction mixture was cooled and subsequently triturated with $Et_2O$/ petroleum benzine. The precipitate was removed by filtration, and the filtrate was concentrated in vacuo to give 2-(p-fluorophenyl)-4-bromomethyl-pyridine (0.63 g, 88%, unstable) as a dark yellow oil.

Q6-Cl:

Scheme A5

The intermediate Q6-Cl was synthesized according to the scheme given below (scheme A5):

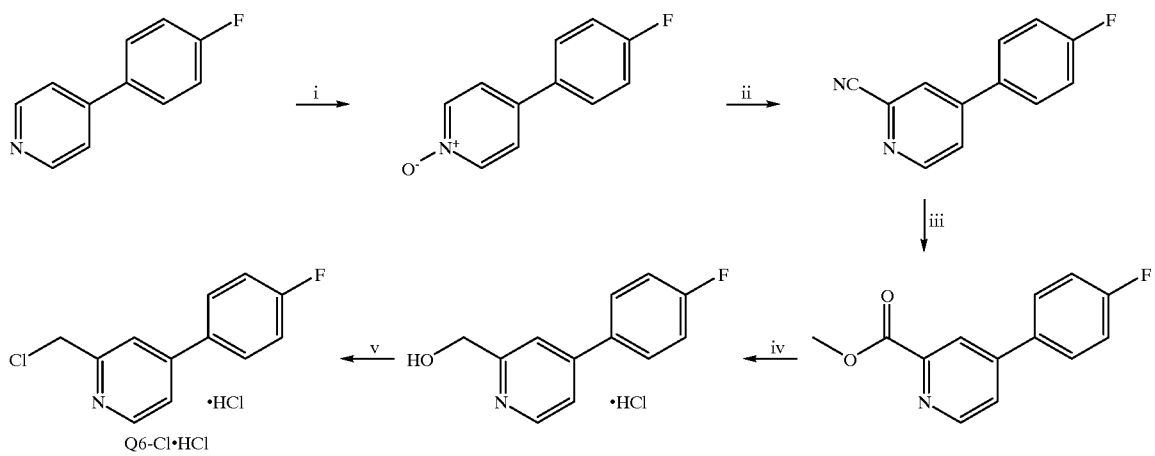

Step i (scheme A5):

4-(p-fluorophenyl)pyridine (13 g, 75 mmol) was dissolved in glacial acetic acid (100%; 50 ml) at 70–80° C. Subsequently $H_2O_2$ (35%; 8 ml) was added while stirring. After 4 hrs an additional portion of $H_2O_2$ (35%; 5 ml) was added. The reaction mixture was allowed to cool after which it was evaporated to dryness in vacuo leaving a yellow solid which was diluted with $H_2O$ (150 ml), basified with an aqueous solution of NaOH (150 ml of a 2M solution), and extracted with $CH_2Cl_2$ (100 ml). The organic layer was separated and dried on $Na_2SO_4$. After removal of the drying agent by filtration and evaporation of the solvent in vacuo, 13 g (91%) of the desired product 4-(p-fluorophenyl)pyridine-N-oxide were isolated.

Step ii (scheme A5):

To 13 g of 4-(p-fluorophenyl)pyridine-N-oxide (68.7 mmol) was added $Me_2SO_4$ (8.6 g, 68 mmol) at 80° C. under an $N_2$ atmosphere after which the mixture was stirred a 100–110° C. for 2 hrs. The mixture was cooled and 70% dioxan/water was poured into the reaction mixture. The obtained dark brown solution was added dropwise to a stirred solution of NaCN (10 g, 0.20 mol) in $H_2O$ (85 ml) at 15–20° C. The mixture was stirred at room temperature for 3 hrs. The reaction mixture was filtered, the residue was washed with $CH_2Cl_2$, which was added to the biphasic filtrate. The organic layer of the filtrate was dried on $Na_2SO_4$. Removal of the drying agent by filtration and evaporation of the solvent in vacuo, yielded the desired compound as a light brown solid which was purified by crystallization from EtOH (300 ml) to provide 2-cyano-4-(p-fluorophenyl)pyridine (8.6 g, 68%): mp 194–195° C.

Step iii (scheme A5):

A stirred solution of 2-cyano-4-(p-fluorophenyl)pyridine (8.6 g, 46.7 mmol) in saturated HCl-MeOH (200 ml) was allowed to react at reflux temperature for 6 hrs. The resulting pink solution was concentrated in vacuo to a volume of approximately 50 ml, after which it was diluted with 250 ml of water. The latter solution was basified with an aqueous solution of $NH_4OH$ (25%), and extracted with $CH_2Cl_2$. The organic layer was dried on $Na_2SO_4$. Removal of the drying agent by filtration and evaporation of the solvent in vacuo, yielded the desired product 4-(p-fluorophenyl)pyridine-2-carboxylic acid methyl ester as a pink solid (5.0 g, 46%): mp 97–8° C.

Step iv (scheme A5):

$NaBH_4$ (8.2 g, 0.2 mol) was added portionwise to a stirred solution of 4-(p-fluorophenyl)pyridine-2-carboxylic acid methyl ester (5.0 g, 21.6 mmol) in EtOH (96%, 100 ml) and the mixture was stirred at room temperature for 6 hrs. The solvent was removed at reduced pressure after which water was added. Subsequently extraction with EtOAc took place. The organic layer was dried on $MgSO_4$. Removal of the drying agent and evaporation of the solvent in vacuo yielded an oil which was dissolved in MeOH and treated with 1.1 eq. HCl/EtOH to afford 2-hydroxymethyl-4-(p-fluorophenyl) pyridinium hydrochloride Q6-OH.HCl as a yellow foam (4.47 g, 87%).

Step v (scheme A5):

This reaction was performed analogously to step iv in scheme A3.

Intermediates used in route B.

Intermediate b1:

This intermediate was synthesized as depicted in scheme B2:

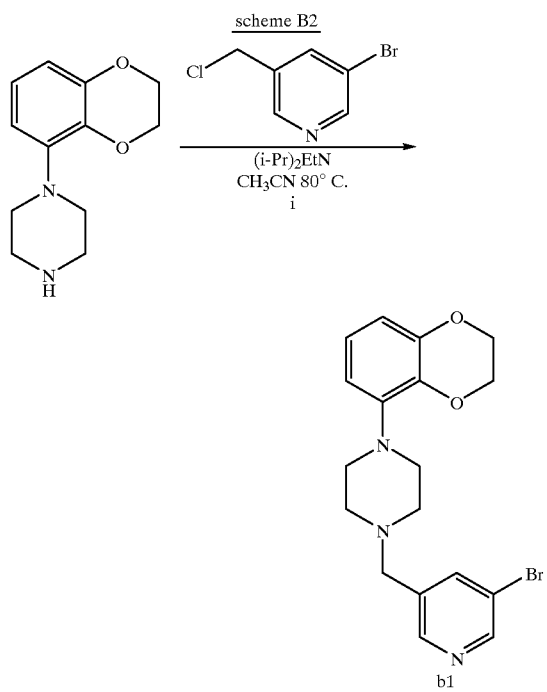

Step i (scheme B2):

To a suspension of 1-(2,3-dihydro-1,4-benzodioxin-5-yl) piperazine monohydrochloride (5.4g, 21 mmol) in CH₃CN (125 mmol) was added 3-bromo-5-chloromethyl-pyridine (4.6 g, 19 mmol) and diisopropylethylamine (12.3 g, 95 mmol). The mixture was stirred at reflux temperature for 30 min. After cooling of the mixture and evaporation of the solvent in vacuo, the residue was taken up in (CH₂Cl₂, washed with 5% NaHCO₃ (aq) solution, saturated NaCl (aq) solution after which the organic fraction was dried on Na₂SO₄. After removal of the drying agent by filtration and solvent by evaporation in vacuo, the residue was purified by flash chromatography on silica gel (CH₂Cl₂/MeOH/ NH₄OH, 97.25/2.5/0.25) to give b1 (7.2 g, 97%) as an oil.

What is claimed is:

1. A compound having the formula (a)

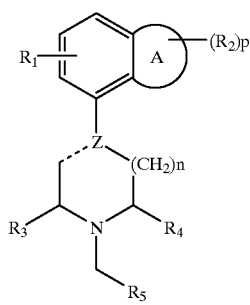

wherein

A represents a heterocyclic group having 5–7 ring atoms wherein 1–3 heteroatoms selected from the group O, N and S are present, $R_1$ is hydrogen or fluoro, $R_2$ is $C_{1-4}$-alkyl, $C_{1-4}$-alkoxy or an oxo group, and p is 0, 1 or 2, Z represents carbon or nitrogen, and the dotted line represents a single bond when Z is nitrogen, and represents a single or double bond when Z is carbon, $R_3$ and $R_4$ independently are hydrogen or $C_{1-4}$-alkyl, n has the value 1 or 2, $R_5$ is 2-pyridyl, 3-pyridyl or 4-pyridyl substituted at the meta-position with respect to the methylene bridge with a group Y, and is optionally substituted with $(R_6)q$, Y is a phenyl, furanyl or thienyl group, which groups may be substituted with 1–3 substituents selected from the group hydroxy, halogen, $CF_3$, $C_{1-4}$-alkoxy, $C_{1-4}$-alkyl, cyano, aminocarbonyl, mono- and di-$C_{1-4}$-alkylaminocarbonyl, $R_6$ is halogen, hydroxy, $C_{1-4}$-alkoxy or $C_{1-4}$-alkyl, and q is 0, 1, 2 or 3, or a pharmaceutically acceptable salt thereof.

2. A compound according to claim 1, wherein A together with the phenyl group represents a group having the formula b, c, d, e, f or g

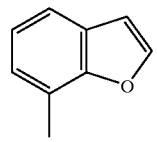
b

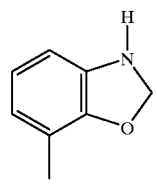
c

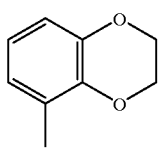
d

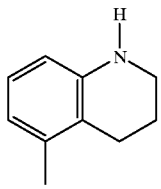
e

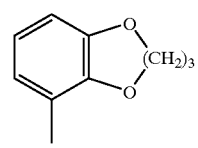
f

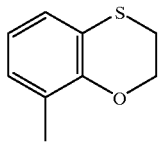
g and wherein n is 1, and $R_1$, $(R_2)p$, $R_3$, $R_4$, $R_5$, $(R_6)q$, Y and Z have the meanings given in claim 1, or a pharmaceutically acceptable salt thereof.

3. A compound according to claim 2, wherein A together with the phenyl group represents a group of the formula (c) or (d), wherein $R_5$ has the meaning given in claim 1, Y is phenyl, $R_3$ and $R_4$ are hydrogen, $R_6$ is hydroxy, methoxy or halogen, q is 0 or 1 and Z is nitrogen, or a pharmaceutically acceptable salt thereof.

4. A compound according to claim 3, wherein A together with the phenyl group represents a group of the formula (d), wherein $R_1$, $(R_2)p$, $R_3$ and $R_4$ are hydrogen, n is 1, Z is nitrogen, and $R_5$ is the group 5-(4-fluorophenyl)-pyrid-3-yl, or a pharmaceutically acceptable salt thereof.

5. A method for preparing a compound of the formula (a) according to claim 1, said method comprising a) reacting a compound of formula

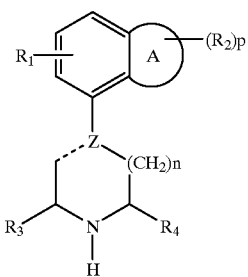

with a compound of the formula $R_5$—$CH_2$—X, wherein X is a leaving group; or b) reacting a compound of the formula

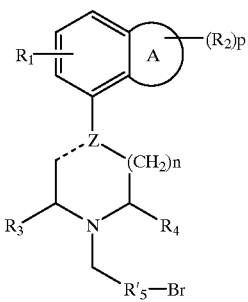

wherein $R_5'$ has the same meaning as $R_5$ as given in claim 1, with the proviso that the bromine atom is at the meta-position with respect to the methylene bridge, with a compound of the formula $B(OH)_2$—Y, in which each substituent has the meanings given in claim 1.

6. A pharmaceutical composition, said composition comprising a pharmaceutically effective amount of at least one compound according to claim 1 and a pharmaceutically acceptable carrier.

7. A method of preparing a pharmaceutical composition for treating a CNS disorder, said method comprising including in said composition a pharmaceutically effective amount of at least one compound of the formula (a) according to claim 1 and a pharmaceutically acceptable carrier.

8. A method of treating a CNS disorder, said method comprising administering to a host in need of said treatment an effective amount of a compound of formula (a) according to claim 1.

9. A compound of the formula

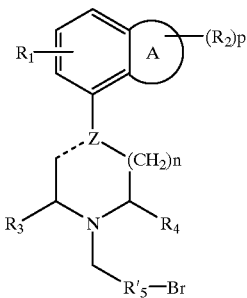

wherein $R_1$, $(R_2)p$, Z, n, $R_3$ and $R_4$ have the meanings given in claim 1, and $R_5'$ has the same meaning as $R_5$ given in claim 1, with the proviso that the bromine atom is at the meta-position with respect to the methylene bridge.

* * * * *